(12) United States Patent
Nambu

(10) Patent No.: US 6,241,670 B1
(45) Date of Patent: Jun. 5, 2001

(54) RADIOTHERAPY SYSTEM

(75) Inventor: Kyojiro Nambu, Tochigi-ken (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/108,538

(22) Filed: Jul. 1, 1998

(30) Foreign Application Priority Data

Jul. 2, 1997 (JP) .................................................. 9-177151

(51) Int. Cl.[7] ....................................................... A61N 5/05
(52) U.S. Cl. .................. 600/427; 600/1; 600/2; 600/3; 378/64; 378/65; 378/138; 378/162; 378/168
(58) Field of Search ................. 378/64, 65, 168, 378/138, 162; 600/407, 427, 1, 2, 3

(56) References Cited

U.S. PATENT DOCUMENTS

| | | | |
|---|---|---|---|
| 5,227,969 | * 7/1993 | Waggener et al. | 128/653.1 |
| 5,704,890 | * 1/1998 | Bliss et al. | 600/1 |
| 5,748,699 | * 5/1998 | Smith | 378/65 |

* cited by examiner

Primary Examiner—Marvin M. Lateef
Assistant Examiner—Jeoyuh Lin
(74) Attorney, Agent, or Firm—Oblon, Spivak, McClelland, Maier & Neustadt, P.C.

(57) ABSTRACT

A radio therapy system includes measuring an actual position of a micro-radiation source and radiation dose actually generated from the source, at predetermined times, during a therapeutic treatment. An accumulative radiation dose distribution is constantly generated in realtime, during the treatment, from the actually measured position and radiation dose and reference radiation dose distribution. An operator can monitor, in realtime, how the radiation dose distribution is developed, temporally, during the treatment. As a result, it is possible to irradiate a lesion with a requisite dose of radiation, minimize any un-required irradiation to a normal area around the lesion and achieve a therapeutic treatment with high precision.

18 Claims, 6 Drawing Sheets

RADIOTHERAPY SYSTEM

BACKGROUND OF THE INVENTION

1. Field of the Invention

The present invention relates to a radiotherapy system for irradiating a lesion of a human subject with a radiation so as to treat the lesion of the subject.

2. Discussion of the Background

Conventionally, the mainstream of the radiotherapy is toward the so-called a treatment through an external irradiation, that is, treating an internal tumor grown in a human subject with a radiation of an external source. However, this treatment has a fear of adversely affecting any healthy region of the subject. Therefore, the radiotherapy was used as an adjunct way of use, such as treating those remnant, not entirely removed, tumor cells by being exposed to a radiation dose of an external source after the surgical opening of the human body, removal of malignant tumors and the suture of the body parts or radiating the radiation dose directly to the remnant tumor cells before the suture of the body parts involved.

However, a recently developed photon radio-surgery system (PRS) is based on a concept of exposing a region of interest (ROI) in the body of the subject to a radiation dose in a controllable fashion while minimizing an adverse effect on the surrounding healthy region. The PRS comprises a PRS probe 1 and control box 3 as shown in FIG. 1. The PRS probe 1 is comprised of an integral unit of a unique X-ray tube 5 and high voltage power source 7. The unique X-ray tube 5 comprises an electron gun 9, electron accelerator 11, deflection coil 13 and a hollow PRS needle 15. Those electrons generated at the electron gun 9 are accelerated to a required every level, properly deflected, passed through the needle 15 in vacuum and finally strike against a film-like target 17 attached to the inside of the tip of the needle 15, that is, an Au target where an X-ray is emitted.

According to the PRS, it is possible to insert the needle 15 from a skin surface side and to emit a radiation at the inside of the target toward a cavity or space created by the evulsion of malignant tumors tumors in the internal organ or tumors in the brain. Therefore, the irradiation of a healthy region with the radiation can be restricted to the surrounding region of the tumor. In addition, any surgical opening can be eliminated or minimized.

For the treatment using the PRS, the most difficult and attentive care problem is a task of, while uniformly irradiating the tumors with a radiation dose, minimizing the irradiation of the surrounding normal (healthy) region with the radiation. Conventionally, the treatment has been progressed in accordance with planning, such as irradiation position and irradiation time, which are determined under a close treatment planning. And it has not been possible to accurately monitor how a radiation dose distribution may be sequentially developed during irradiation.

SUMMARY OF THE INVENTION

It is accordingly the object of the present invention to provide a radio-therapy system which can monitor how a radiation dose distribution is developed with a passage of time during irradiation of a lesion of a human subject with a radiation.

According to the present invention, the actual position of a microradiation source and dose of a radiation actually generated from the microradiation source are measured at each predetermined time during a therapeutic treatment. An accumulative radiation dose distribution is constantly generated, in realtime, during the treatment on the basis of the actually measured position, actually measured radiation dose and reference radiation dose distribution or on the basis of a radiation dose distribution in a predetermined time calculated from the actually measured position and actually measured radiation dose. Therefore, the operator can monitor, in realtime, how the radiation dose distribution is developed, during the treatment, with a passage of time. It is, therefore, possible to, while irradiating a "diseased" region with a requisite radiation dose, suppress an unrequired irradiation of a surrounding region to an extremely low level, and hence to achieve therapeutic treatment with high precision.

According to the present invention, the actual position of the microradiation source and dose of a radiation actually generated from the source are measured at each predetermined time during a therapeutic treatment and sequentially stored. Since the position and radiation dose are so stored, it is possible to generate an accumulative radiation dose distribution at each predetermined time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
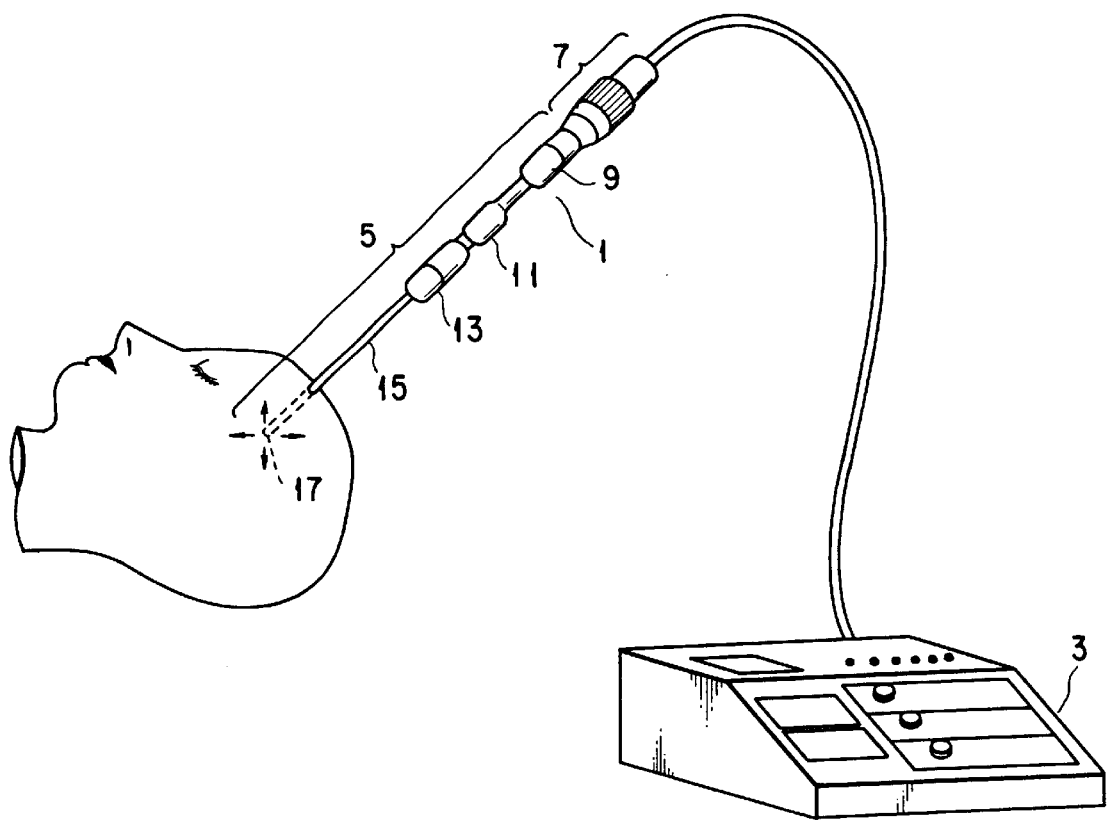
FIG. 1 is an outer view showing a photon radio-surgery system (PRS) is used.

With reference to the drawing, the radio-therapy system will be explained below as a preferred embodiment of the present invention. The most effective application of the present invention is to a photon radio-surgery system (PRS). Here an explanation will be given below about the PRS.

Figure 2:
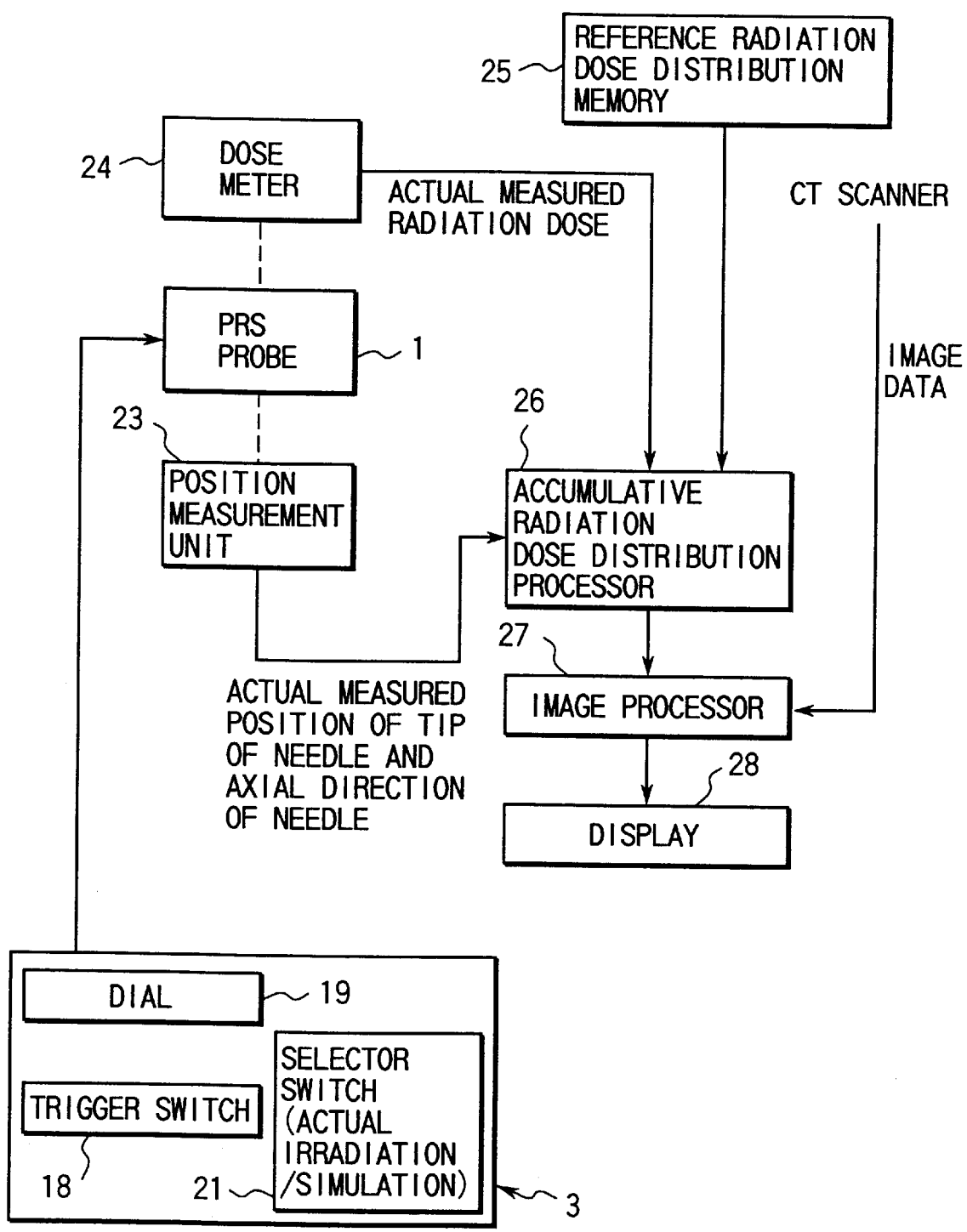
FIG. 2 is a block diagram showing a PRS according to an embodiment of the present invention.

FIG. 2 is a functional block diagram of the PRS according to the present invention. The arrangement of the PRS is the same type as shown in FIG. 1. The PRS comprises a PRS probe 1 and control box 3, as shown in FIG. 1. The PRS probe 1 is comprised of an integral unit of a handy-type unique small X-ray tube 5 and high voltage power source 7. The X-ray tube 5 comprises an electron gun 9, electron accelerator 11, deflection coil 13, and a narrow hollow metal PRS needle of about 3 mm in external diameter X about 2 mm in internal diameter. Electrons are generated from electron gun 9, accelerated to a required energy level, properly deflected, passed through the needle in vacuum and, finally, strike against a film-like Au target attached to the inside of the forward end of the needle 15. An X-ray is emitted with a microradiation source (against which the electron strikes) or a micro-X-ray focal point as a radiation center.

The control box 3 has a trigger switch 18 such as a foot switch (foot pedal). While, for example, the trigger switch 18 is set in the "ON" state by being depressed by the foot of the operator, a high voltage (tube voltage) is applied by the high voltage power source 7 across the electron gun 9 and the target 17 and, by doing so, a radiation is generated from the forward end of the needle 1. While the trigger switch 18 is set in an "OFF" state by being released by the foot of the operator, no high voltage is applied by the high voltage power source 7 and no radiation is radiated.

The control box 3 has a dial 19 for controlling a radiation dose. When the operator turns the dial 19, the tube voltage varies, so that a radiation dose per unit time varies. This control can be freely done during a portion of the radiation time.

Further, the control box 3 has a selector switch 21 (actual irradiation/simulation). With the actual irradiation mode selected, a radiation is actually generated. The simulation mode is selected when a diagnostic planning is taken. With the simulation mode selected, any radiation is actually not generated.

A position measurement unit 23 is so provided as to repeatedly measure the position of the forward tip of the PRS needle 15, that is, the position of the microradiation source, and the axial direction of the needle, that is, the direction of the radiation, at each predetermined time after the start of irradiation. The position measurement may be made by a method as will be set out below.

A dose meter 24 is provided for repeatedly measuring a radiation dose, which is emitted from the tip end of the needle 15, that is, the microradiation source, for each predetermined time at the start of irradiating a radiation. The measurement may be done by a later-described method.

Figure 3:
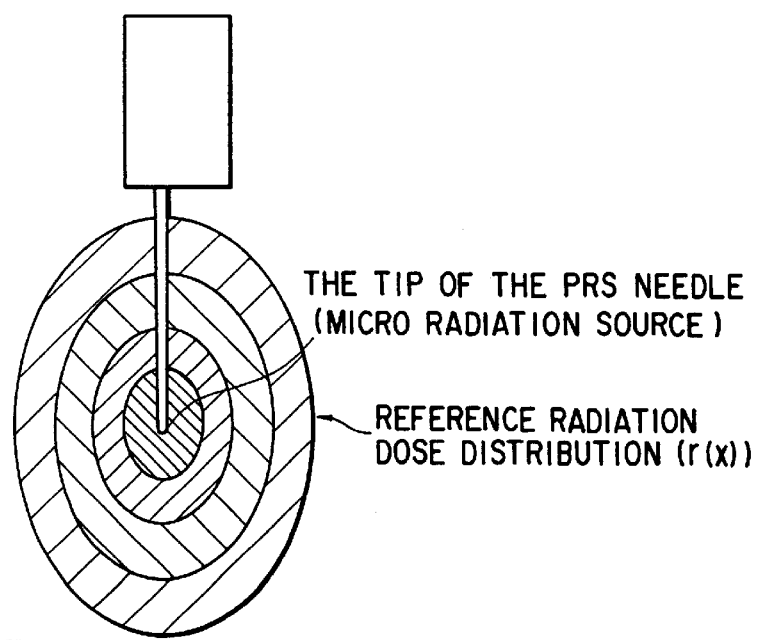
FIG. 3 is a view showing a model of a reference radiation dose distribution stored in a reference radiation source distribution memory of FIG. 2.

As shown in FIG. 3, a reference radiation dose distribution memory 25 initially keeps information on the reference radiation dose distribution. The reference radiation dose distribution represents a spatial distribution of a physical quantity of a radiation absorbed in a living body or in a material such as a water approximate to the living body and corresponds to the case where it is irradiated, with a predetermined radiation dose of source in a unit time. The reference radiation dose distribution may be actually measured using a phantom or may be calculated based on the rule by which the radiation dose in the water is decreased approximately in proportion to a cube of a distance from the radiation dose of source.

It is to be noted that the reference radiation source distribution may be represented by a spatial distribution of a radiation dose in a substantially spherical area or actually represented by a spatial distribution of a radiation dose in a substantially elliptical area elongated in the axial direction of the needle 15 as shown in FIG. 3.

An accumulative radiation dose distribution processor 26 generates, at each predetermined time, an accumulative radiation dose distribution following the start of irradiation with a radiation, on the basis of the position of the microradiation source and axial direction of the needle 15 actually measured by the position measurement unit 23, the radiation dose actually measured by the dose meter 24 and the reference dose distribution stored in the reference radiation dose distribution memory 25. This generating method will be set out below.

An image processor 27 composes an overlay image by superimposing the accumulative radiation dose distribution which is generated by the accumulative radiation dose distribution processor 26 onto an image relating to a lesion and its neighboring tissue, a projection image obtained by an X-ray diagnostic apparatus for example, a cross-sectional image obtained by an X-ray computed tomography apparatus (CT scanner), an MRI image obtained by a magnetic resonance imaging apparatus, and so on. The overlay image processed by the image processor 27 is displayed on a display 28. This display method will be set out below.

An explanation will be given below about the embodiment of the dose meter 24. Here, three kinds of methods are provided as the method of actually measuring a dose of a radiation radiated from the tip end of the needle 15. It may be possible to adopt any of these methods.

(A) This method comprises detecting an actual tube voltage and tube current of the X-ray tube 5 at a time of radiating a radiation and measuring the radiation dose of source on the basis of the detected tube voltage (kV) and tube current ($\mu$A).

Figure 6:
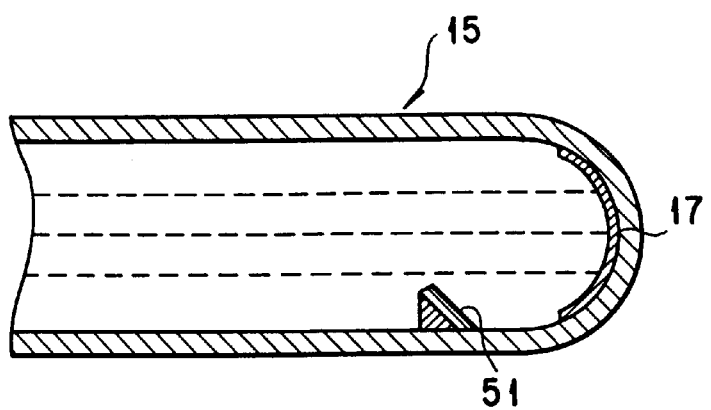
FIG. 6 is an explanatory view showing a first method for measuring a radiation dose by a dose meter of FIG. 2.
Figure 7:
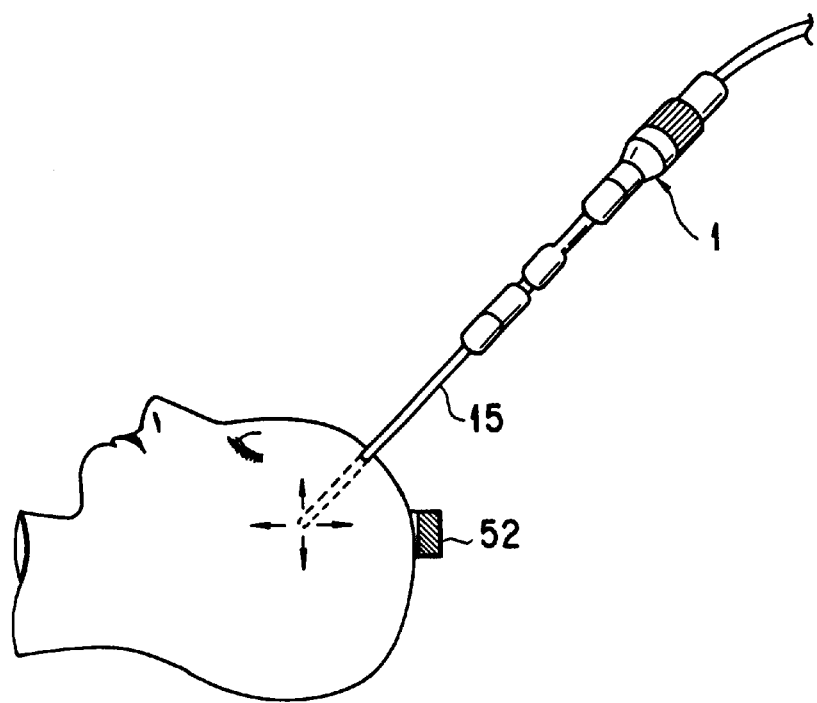
FIG. 7 is an explanatory view showing a second method for measuring a radiation source by the dose meter of FIG. 2.

(B) This method comprises directly measuring an X-ray actually radiated from the radiation dose source at a time of radiating a radiation in the case where a small radiation dose sensor (semiconductor sensor) 51 is provided near the inside of the tip end of the needle 15 along with a mirror 17 as shown in FIG. 6.

(C) This method comprises absorption-correcting a measured value obtained at an outside sensor 52 set outside a patient and approximately finding an X-ray actually radiated from the radiation source at an irradiation time.

Then a practical form of the position measurement unit 23 will be explained below. Here an explanation will be given below about a plurality of practical forms for achieving the position measurement. Of these, any method may be adopted.

(1) Mechanical

Figure 4:
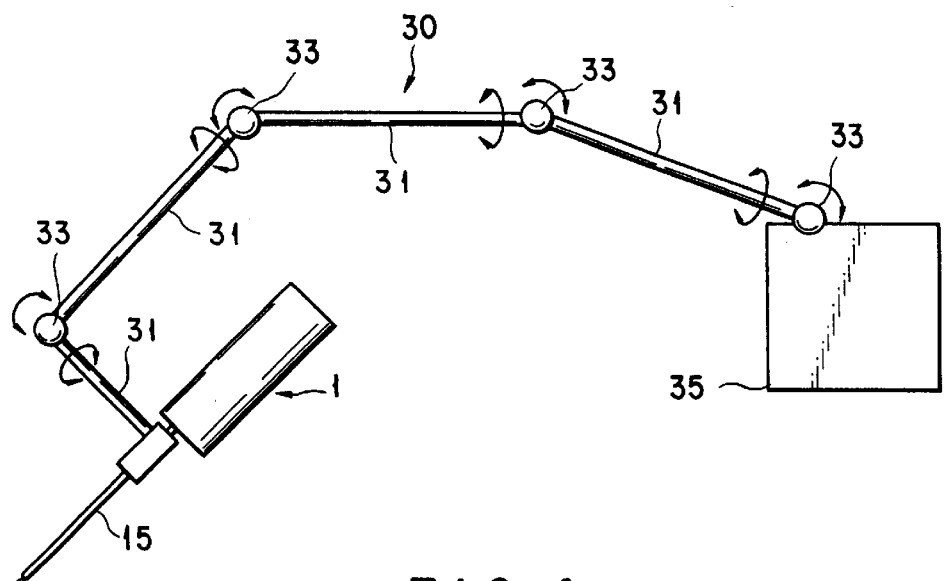
FIG. 4 is an explanatory view showing a first method for measuring a distance by a position measurement unit of FIG. 2.

As shown in FIG. 4, the PRS probe 1 is mounted on the forward end of a multi-articulated arm unit 30. The multi-articulated arm unit has a plurality of arms 31 and a plurality of free joints 33 and is supported on an arm base 35. In the respective free joint 33, two rotary encoders are provided for measuring the rotation angles of two axes orthogonally crossed. The position measurement unit 23 includes a processor for calculating the forward end position (microradiation source) of the PRS needle 15 and axial direction (radiation direction) of the needle 15 on the basis of the rotation angles measured by all the rotary encoders. Of the most recent models, some can measure a position at an accuracy of 0.1 mm to 1 mm or some has a point lock function to allow the axial direction of the needle to be freely shifted without changing the tip position of the needle 15. This mechanical model is characterized in that the tip position of the PRS needle 15 inserted into the patient can be measured with relatively high accuracy. It is to be noted that the multi-articulated arm unit 30 has a secondary advantage of being able to fix the PRS probe 1 in place.

(2) Mechanical

Figure 5:
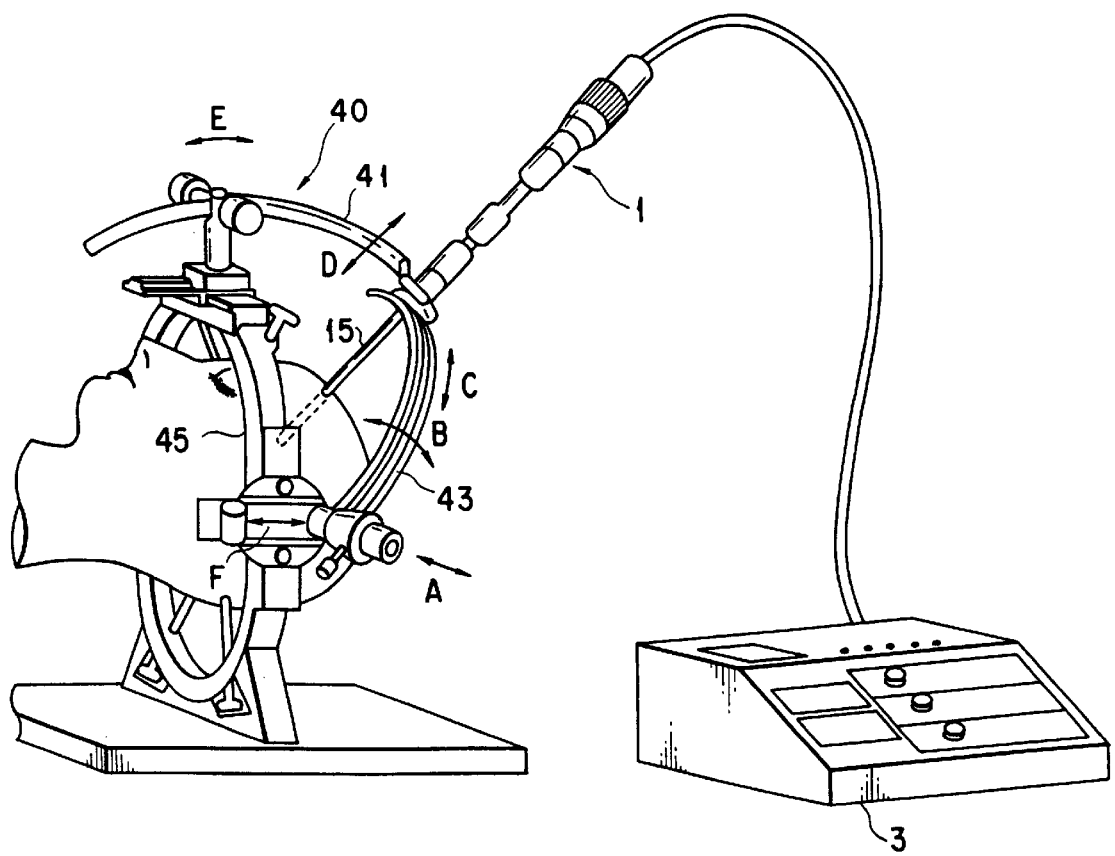
FIG. 5 is an explanatory view showing a second method for measuring a distance by a position measurement unit of FIG. 2.

FIG. 5 shows another mechanical form of the position measurement unit 23. The PRS probe 1 is mounted on a scaling device 40. The scaling device 40 has a location ring 45, such as a location device adapted to be fixed around the head of the patient. Two arms 41, 43 extend from the location ring 45 and the PRS probe 1 may be mounted at a crossing area of the two arms 41, 43. The arms 41, 43 can be freely moved or rotated relative to directions A to F. By doing so, it is possible to insert the needle 15 at any given angle into the patient's head region. The position measurement unit 23 includes a processor for calculating the forward tip position (microradiation source position) of the PRS needle 15 and axial direction (irradiation direction) of the needle 15 on the basis of the output of the rotary encoder corresponding to the directions A to F. This mechanical model is characterized in that it can measure, with relatively high accuracy, the forward tip position of the PRS needle 15 inserted into the patient region. It is to be noted that the scaling device 40 has a secondary effect of being able to fix the PRS probe 1 relative to the patient's head.

Although, in addition to the above-mentioned mechanical models, there are also optical, magnetic and ultrasonic models as will be set out below, the above-mentioned mechanical models may be more of utility in terms of the size, cost, accuracy of the model as well as in terms of a restrictive application otherwise encountered such as it cannot be used at an inserting time.

(3) Optical

In this optical model, optical markers are attached to the forward tip or rear end of the PRS needle 15 and photographed by a plurality of cameras installed in a room in a discrete way. And the forward tip position is calculated on the principle of triangulation. As the optical marker, practical use is made of an infrared light emitting diode (LED), color reflection seal, light scattering sphere, etc. The precision of the optical model is about 0.3 mm for the LED. Upon being compared to the mechanical model, the optical model is excellent in terms of being able to measure a greater number of optical markers at a time. However, it has a drawback in that it is not possible to make measurements if there is any obstacle between the optical marker and the camera.

(4) Magnetical

In this mechanical model, a plurality of coils are arranged in a room in a discrete way and magnetic fields are sequentially generated from these coils in that order. The magnetic fields are detected by a magnetic sensor provided at a proper place of the PRS needle 15 and the forward tip position of the needle 15 is calculated by a comparison made among these detection intensities. Further, a magnetic field may be generated from a coil mounted on a proper place of the PRS needle 15 and detected by a plurality of coils arranged in a room in a discrete way. In this case, the forward tip position of the needle 15 is calculated by a comparison made among the corresponding detection intensities. This magnetic model may involve a greater error if there is any magnetic substance or a good magnetic conductor in its neighborhood. However, this model is practically realized by making a correction through a software for canceling an influence from a static magnetic field. This model can be position-measured even if the forward tip of the PRS needle 15 which is inserted into the patient's region is not seen from an outside.

(5) Ultrasonic

In this ultrasonic model, an ultrasonic wave is generated from a sound source mounted on the PRS needle 15 and received by three or more microphones arranged in a room in a discrete way. By doing so it is possible to calculate the position of the sound source, there is, the forward tip position of the PRS needle 15, from the time differences among the received ultrasonic waves. The precision is of the order of a few millimeters. If, however, there is any influence caused by a variation in sound velocity due to the presence of atmospheric temperature, etc., or there is any obstacle, it is not possible to make measurement or its measurement become lower in accuracy.

By properly selecting or combining these four methods, mechanical, optical, magnetic and ultrasonic, it is possible to achieve accurate position measurement.

Here, the accumulative radiation dose distribution may become useful information once it is composed into an image corresponding to the lesion and its neighborhood. It is, therefore, necessary that the forward tip position and axial direction of the PRS needle 15 represented by a coordinate system inherent in the position measurement unit 5 be converted to a representation by an "operation" room coordinate system with the center of a lesion as an origin. A relation between both the coordinate systems is given by:

$$u = Ax + m$$

where

A: a 3×3 unitary matrix representing a rotation;

m: a 3-dimensional vector representing a translation;

x: a 3-dimensional vector on the forward tip position and direction of the PRS needle 15 represented by the coordinate system inherent in the PRS needle 15; and u: a 3-dimensional vector on the forward tip position and direction of the PRS needle 15 represented by the coordinate system inherent in the "operation" room unit 5.

It is to be noted that A and m are parameters output from the position measuring unit 23. The position measuring unit may be of such a type as to output the position m at the PRS tip inherent in the coordinate system in the "operation" room and direction cosine vector g in the PRS needle.

Figure 10:
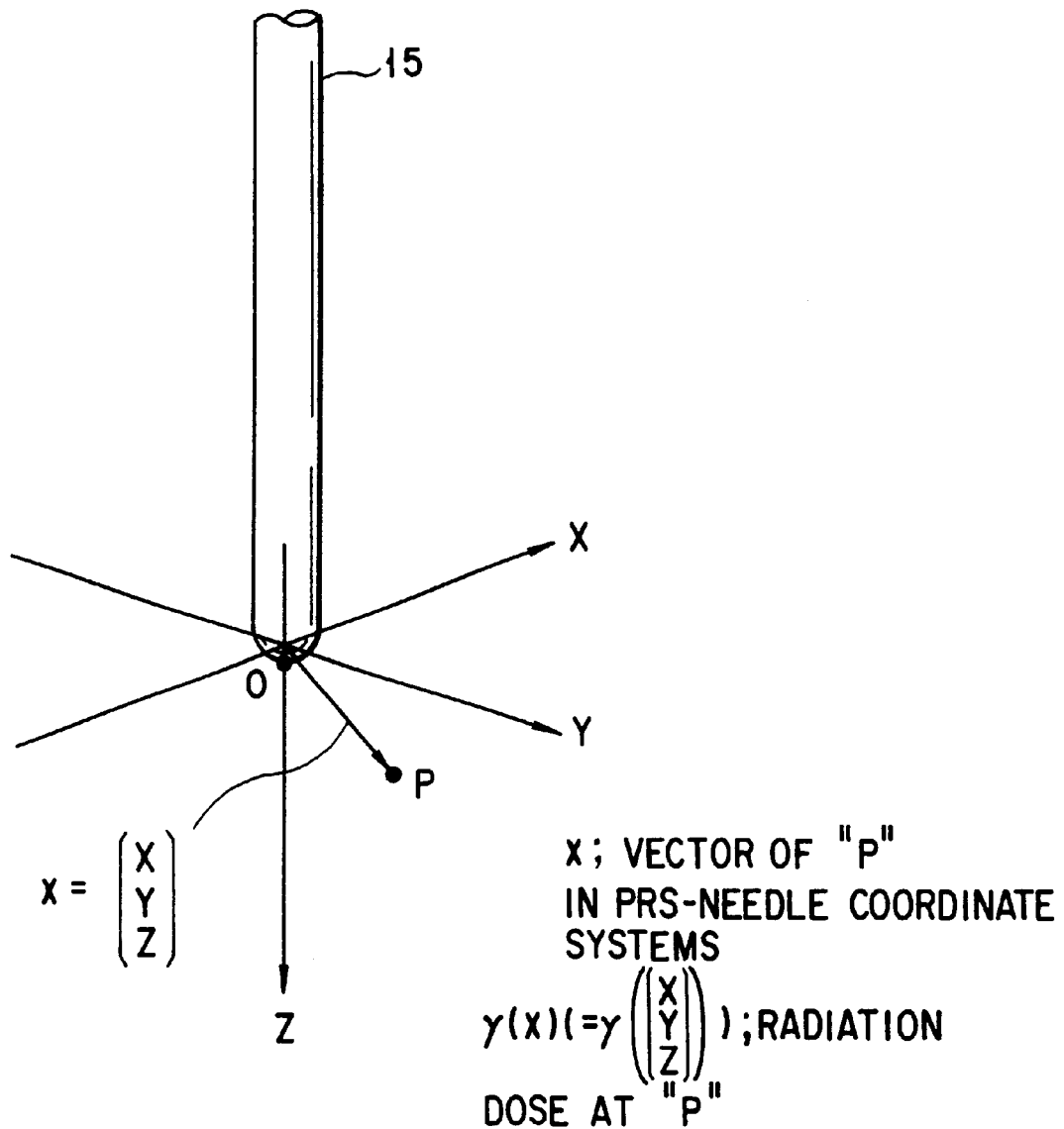
FIG. 10 shows a coordinate system inherent in a PRS needle.

An explanation will be given below about calculating the accumulative radiation dose distribution by the accumulative radiation dose distribution processor 6. As shown in FIG. 10, with x representing a vector from the radiation source a point in a space, the reference radiation dose distribution at the point is given by "γ(x)". When, at a given time "t", the position and direction of the PRS needle 15 are represented by "A(t)x+m(t)" and the measured radiation dose at that time is represented by M times the reference radiation dose provided that M(t)=0 when no radiation is irradiated, then the per-unit-time radiation dose distribution at time "t" is given by $$M(t)r(A(t)x + m(t))$$

Hence, the accumulative radiation dose distribution at a time T passing from a start of an irradiation is given by $$R(x, T) = \int_0^T M(t) r(A(t)x + m(t)) dt \quad (1)$$

If the equation (1) is discretized with a unit time as $\Delta t$, $$R(x, N\Delta t) = \sum_{n=1}^{N} \Delta t M(n\Delta t) r(A(n\Delta t) + m(n\Delta t)) \quad (2)$$

By doing so it is possible to find the accumulative radiation dose distribution with practical precision. Here, the 3-dimensional space is divided into voxels and the accumulative radiation dose R(x,T) at each voxel (position x) can be sequentially found. That is, calculation may be made as follows:

R(x, 0)=0

R(x,n$\Delta$t)=R(x,(n−1)$\Delta$t)+M(n$\Delta$t)r(A(n$\Delta$t)+m(n$\Delta$t))

By the continued calculation of the accumulative radiation dose R(x,T) at each unit time $\Delta t$ it is possible that, even if the position and direction of the PRS needle 15 vary during a portion of an irradiation time or even if the radiation dose in unit time varies, it is possible to calculate an accumulative radiation dose distribution by following such a variation.

If air is present in an area from the PRS needle 15 to the irradiation target such as in an evulsion cavity, in a skin surface or in the lining of the digestive organ, there arises an error in the above-mentioned cumulative radiation dose "R". This is because there is almost no decrease of the radiation dose in air and because the reference radiation dose distribution "r(x)" is actually measured using a phantom with the PRS needle 15 immersed in a physiological salt solution.

Figure 9:
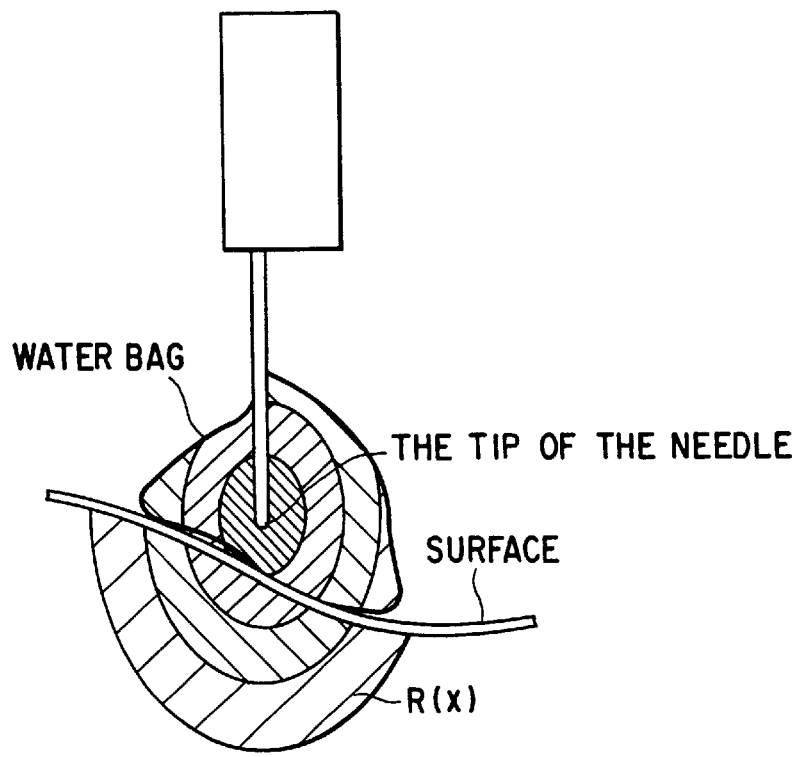
FIG. 9 is a view showing one form of application to the present invention when a lesion of a living body surface is treated under the PRS.

In order to avoid this problem, it is necessary to fill the surrounding of the PRS needle 15 with the physiological salt solution. For the evulsion cavity it is only necessary to fill the cavity with the physiological salt solution. Further, for the skin surface, digestive organ lining, etc., it is only necessary to cover the tip of the PRS needle 15 with, for example, a rubber balloon filled with the physiological salt solution (see FIG. 9). Since a decrease of the radiation in the body tissue of a human subject is almost equal to that in the physiological salt solution except the bone and lungs, it is possible to know the radiation dose with practical precision with the use of the accumulative radiation dose distribution "R".

Now an explanation will be given below about the display method by the image processor 27.

Even if the accumulative radiation dose distribution is known, it is of no practical use unless it is known how it corresponds to the tissue of the patient. That is, the accumulative radiation dose distribution, once being made to correspond to a "lesion" image, provides useful information. For this reason it is necessary to get a "lesion" configuration as set out below in connection with the methods (a) and (b).

(a) Method Using a Position Measurement

By tracing the evulsion cavity or surface of the organ or diseased (lesion) surface of the tract of the digestive organ, etc., by the PRS needle 15, or another special pointer, set in a not-irradiated state, measuring positions on many points on the diseased surface by the position measuring unit 23 and picking up the position information by the image processor 27, it is possible to approximately compose a corresponding surface image, as a polyhedron, from these many points.

As another method, it may be possible to measure the surface configuration by the known surface configuration measuring means, such as a slit camera for photographing light beams scattered on the "tissue" surface after being emitted through the slit, or a moire camera for photographing light beams scattered on the "tissue" surface after projecting a striped pattern with the light beams.

(b) Method Using a Photographing Apparatus

Prior to an operation, or during an operation, in the case where a body surface or a tract of the digestive organ is exposed to light, a picture is taken by an apparatus adapted to photograph a target in a 3-dimensional way, such as an X-ray CT apparatus (CT scanner), magnetic resonance imaging (MRI) apparatus and 3-dimensional ultrasonic cross-sectional apparatus. For this photographing apparatus, it is possible to obtain 3-dimensional image data on the diseased region and, by subjecting the 3-dimensional data to 2-dimensional processing by means of the image processor 27, obtain a surface image gained at (a) or image the broadening of a tissue below a surface. Since, for example, it is possible to know the surface configuration of a "volume" area to be irradiated, it may be composed as an approximate polyhedron. Such 3-dimensional area extraction and modeling are the known technique. Needless to say, the 3-dimensional data obtained by such a 3-dimensional photographing apparatus is supplied directly to the image processor 27 or may be supplied to the image processor 27 via an image keeping device such as a PACS.

The 3-dimensional data thus obtained is used by being converted to a coordinate system inherent in the "operation" room. To this end, it is possible to use those points of a configuration characteristic of the human tissue or markers, such as small metal pieces artificially attached to the human body. That is, such points are extracted among 3-dimensional data by a visual observation or through the image processing and the positions are measured. In the "operations" room, on the other hand, the point positions are measured, by the position measuring unit, as positions in the coordinate system inherent in the "operation" room. Through a linear transform to 3-dimensional data, the 3-dimensional data is subjected to rotation and translation so that such points in the 3-dimensional data are matched to points in the coordinate system inherent in the "operation" room.

Further, an actual irradiation may be simulated, in a simulation irradiation mode not involving the irradiation of a radiation, on the basis of an image of the diseased region by the 3-dimensional photographing apparatus.

Needless to say, use may be made of any given means, such as voxels, for representing a solid configuration in place of the polyhedron.

Now an explanation will be given below about such a display method. Various methods as will be set out below may be considered so as to display a radiation dose distribution using data items on the configuration information of the "diseased" region obtained as set out above.

Figure 8:
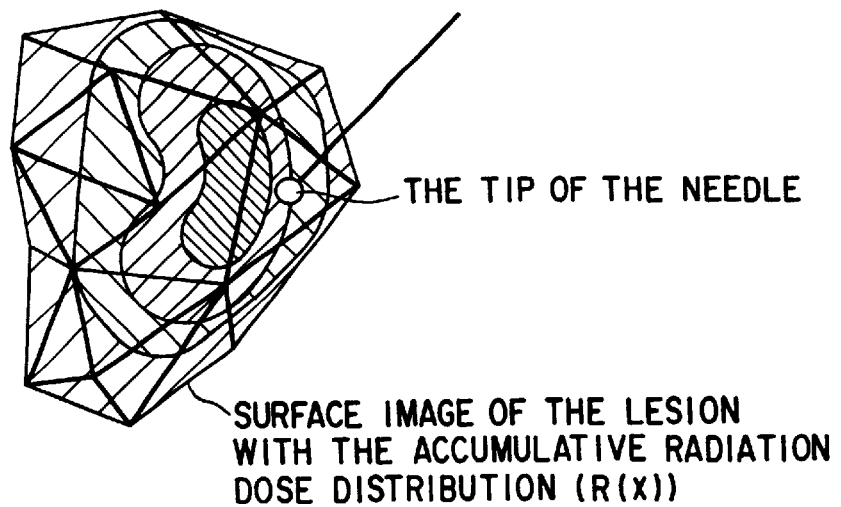
FIG. 8 is a view showing one example of an overlay image composed by an accumulative radiation dose distribution and associated image on a living body.

($\alpha$) This method comprises, as shown in FIG. 8, displaying, by rendering, the surface of a tissue or the surface of a volume area to be irradiated with a radiation and displaying a surface image defined at respective points and marked by a gradation of those colors corresponding to radiation doses at present points. At this time, it is better to display the position and direction of the tip of the needle at the present time points, because the tip of the irradiation needle can be easily and accurately moved nearer to a region to be irradiated with the radiation.

($\beta$) A display method using an augmented reality is also known. As disclosed in JPN PAT APPLN KOKOKU PUB- LICATION NO. 6-85784 relating to a 3-dimensional viewer system for a surgical operation, it may be possible to superimpose a real image on an accumulative radiation dose distribution and display a corresponding image. The real image is obtained by an optical device such as a video camera or a surgical operation microscope of low power and the accumulative radiation dose distribution image is superimposed onto the real image by an electrical or optical means. At this time, the position and direction of the real image obtaining means are measured by a position measurement unit 5 of a type as set out above. By doing so, while matching such a real image to an observing direction, a radiation dose distribution image as viewed from that direction is created by the image processor 27. As the radiation dose distribution image displayed here, use can be made of an image as set out in connection with the method ($\alpha$).

($\gamma$) An accumulative radiation dose distribution, not the one on a surface, may be displayed using a projection image or cross-sectional image. In this case, it may also be done in a way to be superimposed on respective ones of a plurality of projection images or cross-sectional images differing in a projection direction or cross-sectional position. By doing so, they are displayed at a time and are desirable because it is possible to provide 3-dimensional information.

($\delta$) The tissue configuration and distribution may be displayed, as a 3-dimensional image, on various 3-dimensional display devices.

Next an explanation will be given below about the simulation for making diagnostic planning. The present embodiment provides a simulation of "a variation, with time, of the accumulative radiation dose distribution". This simulation is useful in the case where there is a fear of any normal region around a "lesion" being irradiated with a radiation. The simulation can be realized by supplying the information on the planned radiation dose, radiation dose position and axial direction, not the actually measured radiation dose, radiation source position and axial direction, to the accumulative radiation dose distribution processor 26.

This simulation can be preliminarily practised in real-time and it is possible to control, for example, a per-unit-time radiation dose to a proper level and confirm the position or direction of the radiation source, irradiation time, etc. With the PRS needle 15 attached to the forward end of the robot arm, it is possible to, as simulated, vary the per-unit-time radiation dose level and the position and direction of the radiation dose, timewise, to place this process onto a way toward a full automation.

According to the present embodiment it is possible to measure the actual position of the microradiation source and actual radiation dose level from this source, during a treatment, at each predetermined time. The accumulative radiation dose distribution is momentarily created, during the treatment, in real-time on the basis of the actually measured position and radiation dose level and the reference radiation dose distribution or on the basis of a radiation dose distribution in a predetermined time calculated from the actually measured position and dose level. Therefore, the operator can monitor a temporary broadening of the radiation dose distribution, during the treatment, in real-time. It is, therefore, possible to, while irradiating the lesion with a requisite amount of radiation, make the irradiation of a normal region around the lesion at a necessary lowest radiation dose level and hence to achieve a treatment with high precision.

The present invention is not restricted to the above-mentioned embodiment. Various changes or modifications of the present invention can be made without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radio-therapy system for irradiating a lesion of a subject with a radiation so as to treat the lesion, comprising:
    means for radiating the radiation from a microradiation source, the microradiation source being located inside, or near to, the lesion so as to irradiate the lesion with the radiation;
    position measuring means for measuring a position of the microradiation source;
    dose measuring means for measuring a dose of the radiation radiated from the microradiation source;
    storing means for storing information on a reference radiation dose distribution, the reference radiation dose distribution representing a spatial distribution of a physical quantity of radiation absorbed in a living body of a subject or in a material approximating the living body and corresponding to a case where a radiation is radiated, for a unit time, at a predetermined source dose;
    generating means for generating an accumulative radiation dose distribution on the basis of a measured microradiation source position, measured radiation dose and stored reference radiation dose distribution, the accumulative radiation dose distribution being related to the lesion and area around the lesion; and
    display means for displaying the generated accumulative radiation dose distribution,
        wherein the stored reference radiation dose distribution displays a spatial variation of the radiation dose in a spherical area or an ellipsoid of revolution.

2. The system according to claim 1, wherein the radiating means includes an X-ray tube including an electron gun and hollow needle,
    electrons are emitted from the electron gun, past an inside of the needle, at a target provided inside a tip of the needle, and
    the radiation is generated from the tip of the needle.

3. The system according to claim 2, wherein the position measuring means measures the position of the microradiation source and direction of the needle.

4. The system according to claim 3, wherein the stored reference radiation dose distribution represents a spatial distribution of the radiation in a substantially elliptical area, and
    the generating means generates the accumulative radiation dose distribution such that a major axis of the reference radiation dose distribution corresponds to the direction of the needle.

5. The radio-therapy apparatus according to claim 2, wherein the dose measuring means has means for detecting a tube voltage and tube current of the X-ray tube and means for calculating a dose of the radiation radiated from the target on the basis of the detected tube voltage and tube current.

6. The radio-therapy system according to claim 2, wherein the dose measuring means has a radiation sensor located, inside the needle, in a position near to the target and means for calculating a dose of the radiation radiated from the target on the basis of an output of the radiation sensor.

7. A radio-therapy system according to claim 1, wherein the display means displays the accumulative radiation dose distribution in a way to be superimposed on a projection image relating to the lesion and area around the lesion, on a cross-sectional image or a 3-dimensional image relating to the lesion.

8. The system according to claim 7, wherein the displaying means displays the accumulative radiation dose distribution with a gradation added thereto in color corresponding to the radiation dose or a contour line.

9. The system according to claim 7, wherein the displaying means simultaneously displays the accumulative radiation dose radiation with a plurality of projection images or cross-sectional images differing in projection direction or in cross-sectional position, respectively.

10. The system according to claim 1, wherein the position measuring means has a multiarticulated arm unit for supporting the microradiation source and means for calculating a position of the microradiation source on the basis of angles of joints in the multi-articulated arm unit.

11. The radio-therapy system according to claim 1, wherein the position measuring means has a plurality of scales adapted to be set to the subject in a state associated with the microradiation source and means for calculating a position of the microradiation on the basis of the plurality of scales.

12. The system according to claim 1, wherein the dose measuring means has a radiation sensor located outside the subject and means for calculating a dose of the radiation radiated from the target on the basis of the output of the radiation sensor.

13. The system according to claim 1, wherein the generating means has the function of generating an accumulative radiation dose distribution on the basis of a planned position and planned dose of the microradiation source and reference radiation dose distribution, based on a simulation for establishing therapy planning without actually radiating the radiation.

14. The system according to claim 1, further comprising means for approximately generating a surface image of the lesion as a polyhedron on the basis of the positions of a plurality of points on the surface of the lesion measured by the position measuring means.

15. A radiation-therapy system for irradiating a lesion with a radiation so as to treat the lesion, comprising:

means for radiating the radiation of a microradiation source, the microradiation source being located inside, or near to, the lesion so as to irradiate the lesion with the radiation;

position measuring means for measuring the position of the microradiation source;

dose measuring means for measuring a radiation dose from the microradiation source;

means for storing a position and radiation dose of the microradiation source; and display means for displaying a generated accumulative radiation dose distribution based on a stored reference radiation dose distribution, wherein the reference radiation dose distribution displays a spatial variation of the radiation dose in a spherical area or an ellipsoid of revolution.

16. The apparatus according to claim 15, further comprising:

storing means for storing information relating to the reference radiation dose distribution, the reference radiation dose distribution representing a spatial distribution of a physical quantity of a radiation absorbed in a living body or a material approximating the living body and corresponding to a case where a radiation is radiated, in a unit time, with a predetermined dose; and generating means for generating the accumulative radiation dose distribution on the basis of the position of the microradiation, stored radiation dose and stored reference radiation dose distribution.

17. A radio-therapy system for irradiating a lesion with a radiation so as to treat the lesion, comprising:

radiating means for radiating the radiation from a microradiation source, the microradiation source being located inside, or near to, the lesion of the human subject so as to irradiate the lesion with the radiation from the microradiation source;

position measuring means for measuring a position of the microradiation source;

dose measuring means for measuring a dose of the radiation;

generating means for, based on the position of the measured microradiation and radiation dose, generating an accumulative radiation dose distribution relating to the lesion or a neighborhood of the lesion and based on a stored reference radiation dose distribution; and display means for displaying the generated accumulative radiation dose distribution, wherein the stored reference radiation dose distribution displays a spatial variation of the radiation dose in a spherical area or an ellipsoid of revolution.

18. The system according to claim 17, wherein the generating means includes means for, with a position of the measured radiation dose as a center, calculating the radiation dose distribution in accordance with a distance from that center and means for, in order to generate an accumulative radiation dose distribution, accumulating the calculated radiation dose distributions.

* * * * *